United States Patent [19]

Lebens

[11] Patent Number: 5,745,176
[45] Date of Patent: Apr. 28, 1998

[54] MACHINE-VISION ILLUMINATION SYSTEM AND METHOD FOR DELINEATING A LIGHTED VOLUME FROM AN UNLIGHTED VOLUME

[75] Inventor: Gary A. Lebens, Chaska, Minn.

[73] Assignee: PPT Vision, Inc., Eden Prairie, Minn.

[21] Appl. No.: 532,213

[22] Filed: Oct. 12, 1995

[51] Int. Cl.$^6$ ............................ H04N 7/18; H04N 9/47; H04N 5/222
[52] U.S. Cl. .................. 348/370; 348/131; 348/132; 359/739; 362/244; 362/248; 235/462
[58] Field of Search ...................... 359/738, 739; 362/234, 235, 236, 244, 248; 348/86, 87, 370, 371, 125, 126, 127, 128, 131, 132; 235/454, 462; H04N 5/222, 7/18, 9/47

[56] References Cited

U.S. PATENT DOCUMENTS

| | | | |
|---|---|---|---|
| 3,663,752 | 5/1972 | Froschle | 178/7.2 |
| 4,743,773 | 5/1988 | Katana et al. | 250/566 |
| 4,882,498 | 11/1989 | Cochran et al. | 250/571 |
| 4,972,093 | 11/1990 | Cochran et al. | 250/572 |
| 5,010,412 | 4/1991 | Garriss | 358/240 |
| 5,051,825 | 9/1991 | Cochran et al. | 358/106 |
| 5,072,127 | 12/1991 | Cochran et al. | 250/572 |
| 5,172,005 | 12/1992 | Cochran et al. | 250/57 |
| 5,354,977 | 10/1994 | Roustaei | 235/472 |
| 5,468,950 | 11/1995 | Hanson | 235/472 |
| 5,604,550 | 2/1997 | White | 396/429 |

OTHER PUBLICATIONS

Hewlett Packard OptoElectronics Designer's Catalog, Technical Data entitled "High power AlInGaP Amber and Reddish–Orange Lamps," pp. 3–24 through 3–29, 1993.
Edmund Scientific Company 1993 Annual Reference Catalog, "Cylinder Lenses (CYL)"; catalog pp.47.

Primary Examiner—Thai Tran
Assistant Examiner—Ngoc-Yen Vu
Attorney, Agent, or Firm—Schwegman, Lundberg, Woessner & Kluth P.A.

[57] ABSTRACT

The present invention takes advantage of the efficiency of high-brightness red, infra-red, or other color LEDs arranged in a single row, the properties inherent to a focusing element such as a cylindrical lens, as well as the advantages of having a straight-edged diaphragm and a light-absorbing enclosure to produce an illumination source for machine-vision systems. The illumination source exhibits multi-directional properties on one side of an imaginary plane defined by the positions of the row of LEDs, the straight-edged diaphragm, and the focusing element, and minimize light cast on the other side of the plane. The present invention provides a compact light line generator which has no shadowing or secondary lines. The present invention also provides a method for measuring the height of a raised surface. The present invention provides a method and apparatus which provide an illumination source for illuminating an object in a machine-vision system, and includes a light source emitting light from a plurality of points, the points being on a straight line, a focusing element, the focusing element focusing light from the light source in one dimension to a focal line, wherein the focusing element is separated from the straight line by a distance sufficient to focus rays from the plurality of points into the focal line, and wherein there is a light path from the straight line to the focusing element and then to the focal line, and a first diaphragm located in the light path and defining a sharp edge in the rays. This embodiment provides a light which has a sharply defined virtual surface which separates lighted areas from areas not lit, and within the lighted areas, provides light from multiple directions to reduce shadowing.

24 Claims, 8 Drawing Sheets

MACHINE-VISION ILLUMINATION SYSTEM AND METHOD FOR DELINEATING A LIGHTED VOLUME FROM AN UNLIGHTED VOLUME

TECHNICAL FIELD OF THE INVENTION

The present invention pertains generally to optics and more particularly systems and methods for illumination of objects in machine-vision systems.

BACKGROUND OF THE INVENTION

During the manufacture of certain products, such as electrical connectors, it is necessary to be able to provide high-intensity illumination so that components can be thoroughly inspected with a machine-vision system. Well-defined high-intensity illumination is also useful as a measuring tool when used in combination with a machine-vision system. On the other hand, certain systems and methods for providing illumination for machine-vision systems cause "bloom" (i.e., wherein, in order to provide enough light in one area of interest in the field of view of the video camera, too much light ends up on another area in the field of view, causing an over-exposure which results in loss of resolution or visibility to the area of interest) in the machine-vision-system camera.

Typically, a fiber-optic-based or laser-based single-point source is used for these purposes. A fiber-optic-based source is typically coupled to a xenon flash tube or other high-intensity light source. Such systems, however, are costly, very large and bulky, and can interfere with the placement of other components in the machine-vision system. This is particularly troublesome when the components being measured or inspected are extremely small. Xenon flashtube light sources also tend to exhibit up to about a five per cent (5%) flash-to-flash variation in intensity which makes accurate measurements of certain characteristics difficult. Single-point source systems are also generally limited to emitting light radially from only one single point, which is of limited value when shadows are problematic, such as, when inspecting a grid of electrical connectors. Specifically, light from a point source or distant source (i.e., having only parallel rays) only illuminates the first over-sized or over-height electrical connector and does not provide proper illumination which would determine if other connectors behind this particular first connector are missing, of the incorrect size or height, or perhaps in the wrong position.

Conventional illumination systems produce a light which illuminates too broad of an area or areas which should not be illuminated, and can also be too bright in certain areas and too dim in other areas. Often, the end-result is "bloom", especially when viewing white, lightly colored, or very reflective objects which are near other objects which need to be viewed by a machine-vision camera. In order to get enough light on the other objects which need to be viewed, the aperture on the camera cannot be "stopped down" in order to prevent overexposure of the bright objects. Specifically, the area is illuminated to such an extent that the entire image appears to be the same bright saturated white color (or, if a monochromatic light source is used, saturated at whatever color is used) as viewed by the machine-vision camera and system. Such extreme brightness also poses a danger of blinding, at least temporarily, human workers nearby.

Quite often, illumination sources either leave certain portions of the scene in shadows, or provide too much light in certain areas, while leaving other areas with too little light. In other cases, the illumination source is too bulky and gets in the way of other components of the machine-vision system, associated robots, manipulators, and/or human workers.

Thus, what is needed is an illumination system and method which is compact, generates a light ray from more than one source with suitable brightness, focuses the light ray into a sharp source in one dimension (e.g., horizontally) and a diffuse source in another dimension or dimensions (e.g., vertically, or vertically and longitudinally), so that even extremely small parts can be adequately inspected and accurately viewed or measured with a machine-vision system. Another need is to provide a compact illumination source, preferably monochromatic, which can be focused to provide uniform multi-directional light onto objects on one side of an imaginary plane, while minimizing light on the other side of that plane. Another need is to provide a compact monochromatic LED (light-emitting diode) illumination source, which can be focused to provide uniform multi-directional light onto objects on one side of an imaginary plane, while minimizing light on the other side of that plane. Another need is to have such an LED illumination source be pulsed with a relatively high-power, low duty-cycle power source.

SUMMARY OF THE INVENTION

The present invention takes advantage of the efficiency of high-brightness red, infra-red, or other color LEDs arranged in a single row, the properties inherent to a focusing element such as a cylindrical lens, as well as the advantages of having a straight-edged diaphragm and a light-absorbing enclosure to produce an illumination source for machine-vision systems. The illumination source exhibits multi-directional properties on one side of an imaginary plane defined by the positions of the row of LEDs, the straight-edged diaphragm, and the focusing element, and minimize light cast on the other side of the plane. The illumination very nearly resembles a line of point sources of light which is useful for illumination of small components (which are being inspected or measured) without unwanted shadows. Another embodiment of the present invention uses a strobed (or pulsed) power supply to drive the LEDs. Yet another embodiment of the present invention uses a xenon strobe light source and a backplane slit in place of the row of LEDs 25. In one such xenon strobe embodiment, a color filter is also placed in series with the light path in order to obtain a monochromatic light. While xenon flashtube light sources tend to exhibit a five per cent (5%) flash-to-flash variation in intensity which makes accurate measurements of certain characteristics difficult, they are useful in certain cases where intense white, or especially ultraviolet, light is desired.

The present invention provides a compact light line generator which has little, is any, shadowing or secondary lines. The present invention also provides a method for measuring the height of a raised surface.

The present invention provides a method and apparatus which provide an illumination source for illuminating an object in a machine-vision system. One embodiment of the illumination source includes a light source emitting light from a plurality of points, the points being on a straight line, a focusing element, the focusing element focusing light from the light source in one dimension to a focal line, wherein the focusing element is separated from the straight line by a distance sufficient to focus rays from the plurality of points into the focal line, and wherein there is a light path from the straight line to the focusing element and then to the focal line, and a first diaphragm located in the light path and defining a sharp edge in the rays. This embodiment provides a light which has a sharply defined virtual surface which separates lighted areas from areas not lit, and within the lighted areas, provides light from multiple directions in order to reduce shadowing.

Another embodiment of the present invention uses a first diaphragm having at least one straight-line segment parallel to the straight line of the light source. Yet another embodiment includes an enclosure having an interior surface which is anti-reflective at a wavelength of the light source, the straight line of the light source being located inside the enclosure. One such embodiment uses a light source which includes at least one light-emitting diode (LED), which can be infra-red, red, amber, yellow, green, or blue in color. One such embodiment uses LEDs wherein the light emitted from the LEDs is at an angle of about 22.5° from a center line of each individual LED.

One embodiment uses a focusing element which is a plano-convex cylindrical lens having a flat surface and a cylindrical surface.

Another embodiment further includes a second straight-edged diaphragm located adjacent the flat surface of the cylindrical lens to reduce reflections from the light source.

These and other features, aspects, and advantages of the present invention will become better understood with regard to the following description, appended claims and accompanying drawings.

BRIEF DESCRIPTION OF THE DRAWINGS

FIG. I 0 is a block diagram of the electrical connections for machine-vision illumination system 100.

DETAILED DESCRIPTION OF THE INVENTION

In the following detailed description of the preferred embodiments, reference is made to the accompanying drawings which form a part hereof, and in which are shown, by way of illustration, specific embodiments in which the invention may be practiced. It is to be understood that other embodiments may be utilized and structural changes may be made without departing from the scope of the present invention.

The present invention provides a method and system for generating rays of light with suitable brightness from more than one source. The rays are focused into a sharp source horizontally and a diffuse source vertically such that even extremely small objects can be adequately inspected and accurately measured by a machine-vision system 100.

The unique ability of the method and apparatus of the LED illumination system of the present invention to provide a light source within these constraints distinguishes this system from other commercially available illumination systems purporting to provide suitable high-intensity illumination for inspecting or measuring purposes.

Figure 1A:
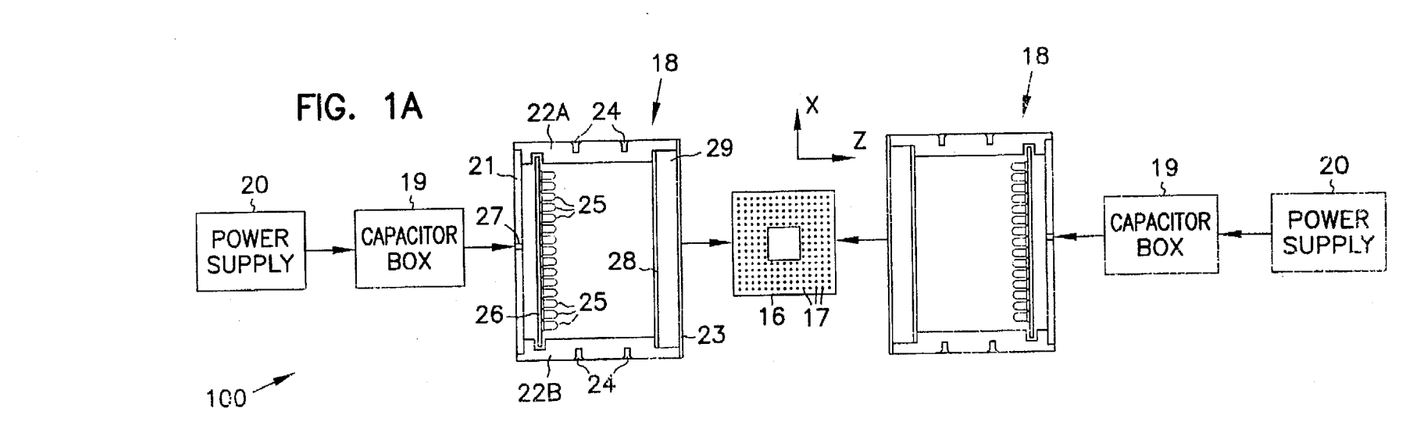
FIG. 1A is a top-view schematic diagram of an embodiment of machine-vision illumination system 100 of the present invention.
Figure 1B:
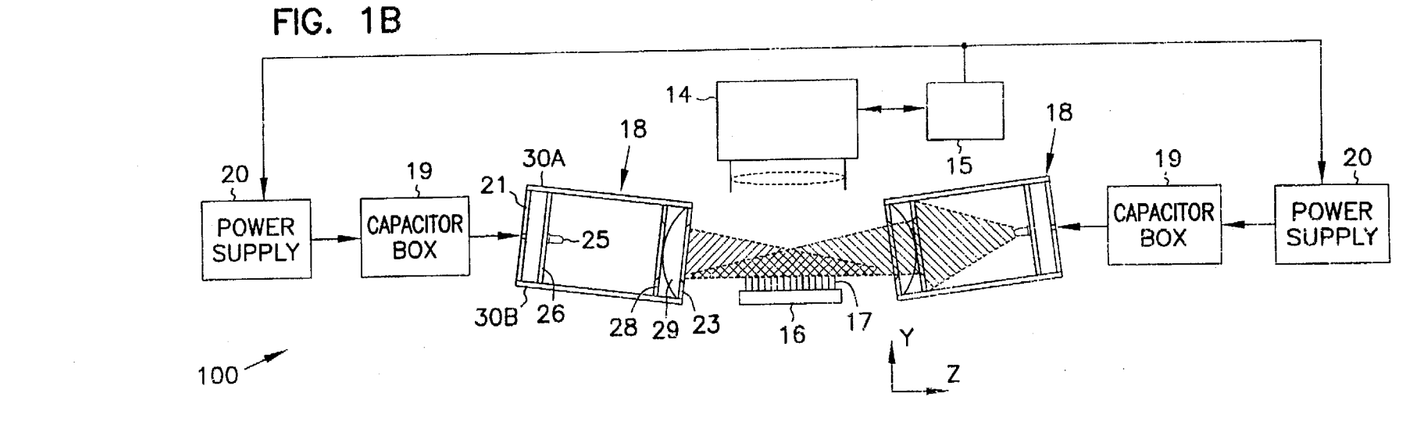
FIG. 1B is a side-view schematic diagram of an embodiment of machine-vision illumination system 100.

FIG. 1A shows a top view and FIG. 1B shows a side view of one embodiment of machine-vision illumination system 100 of the present invention, wherein an object 16 (a pin-grid array socket having pins 17) is illuminated for inspection by a machine-vision imaging device 14 and image processor 15. In the exemplary system shown, it is desired to illuminate the tips of pins 17 for viewing by imaging device 14 without illuminating the rest of object 16. In one embodiment, machine-vision system 100 comprises an imaging device 14 which is coupled to image processor 15. In one embodiment imaging device 14 is a video camera, such as a Panasonic model GPMF702, having a telecentric lens, such as an Invaritar-brand lens made by Melles-Griot. In one such embodiment, the telecentric lens, which has uniform magnification across the field of view, of imaging device 14 is made larger in diameter than the diameter of object 16 being viewed (e.g., one embodiment uses a 6-inch diameter lens for 3-inch diameter objects) in order to reduce lens distortion, such as pincushioning and barrel distortion. Imaging device 14 is coupled to image processor 15 with suitable cables, for example electrical or fiber-optical signal cables. Imaging device 14 is positioned above and facing the pins of the pin-grid array, i.e., object 16 having electrical connector pins 17, so that imaging device 14 can obtain a captured image of the electrical connector pins 17.

Imaging device 14 can be implemented as any one of a number of device technologies including vidicon, CCD (charge-coupled device) line- or array-imaging devices, MOS video cameras, x-ray detectors, and so forth. In one embodiment, imaging device 14 is a solid-state video camera. In one such embodiment, imaging device 14 is a solid-state MOS camera having a peak wavelength sensitivity of about 550 nanometers (nm), and range of approximately 500 to 600 nm at about 97% of peak. In one embodiment, the aperture on the lens of imaging device 14 is suitably small in order that a relatively large depth of-field is obtained. In one embodiment, a telecentric lens is used. The type and size of lens is chosen to match the field-of-view to the size of object 16.

In one embodiment, electrical connector pins 17 are typically shiny gold-plated metal contacts, and are illuminated by a suitable number of (i.e., one or more) illumination sources 18. In FIG. 1A and 1B, two illumination sources 18 are used on either side of the socket 16 of electrical connectors 17 for this purpose, although any suitable number of illumination sources 18 can be used. Each illumination source 18 may be moved up and down relative to object 16 in order to provide illumination for the machine-vision system 100, for example so that it can be determined if each electrical connector 17 is in the proper position in the X and Z direction, as well as the correct height in the Y direction. For example, when illumination source 18 is positioned at a Y height corresponding to the maximum allowable pin height, only the pins which are too high will be illuminated; when illumination source 18 is positioned at a Y height corresponding to the minimum allowable pin height, only the pins which are too low will not be illuminated. Thus, the sharp edge of the plane separating light from dark (created by one or both of diaphragms 23 and 28, and focusing element 29) can be used to optically measure the heights of the pins and determine which are out-of-tolerance. In one embodiment, the edge between light and dark is merely positioned to avoid lighting areas which it is desired not to light, while providing light on other areas.

In one embodiment, each illumination source 18 is connected to a capacitor box 19, which is connected to a power supply 20, which is connected to image processor 15. In the embodiment shown in FIGS. 1A and 1B, each illumination source 18 is enclosed to light except for the opening through lens 26, and includes back cover plate 21 on one end connected to two side plates 22A and 22B; side plates 22A and 22B are also connected to a front straight-edged diaphragm 23 located on the front side of a lens 26 and on the end opposite back cover plate 21. Top cover 30A and bottom cover 30B complete the enclosure.

In one embodiment, all interior surfaces of illumination source 18 including the side plates 22A and 22B, top and bottom covers 30A and 30B, circuit board 26, and back cover plate 21 have an anti-reflective (e.g., flat black) surface to prevent reflections. In one embodiment, the flat black surface is obtained by applying flat black paint, for example speckle-painted flat-black paint. In another embodiment, the flat black surface is obtained through use of a standard black anodization process which subjects the metal surfaces of side plates 22A and 22B, top and bottom covers 30A and 30B, and back cover plate 21 to electrolytic action, in order to coat them with a flat black film. In one embodiment, additional baffles (not shown) are provided along the light path between LEDs 25 and object 16 in order to minimize reflected LED light. In one embodiment, a shroud having a flat black interior surface is also provided around some (e.g., in the case where it is desired to have a human user view to object 16, in addition to imaging device 14), or all (in the case where only imaging device 14 views object 16), of the light path between object 16 and imaging device 14 in order to minimize reflected LED light and/or unwanted ambient light.

Furthermore, in the embodiment shown in FIGS. 1A and 1B, each side plate 22A and 22B has two screws which are inserted into mounting holes 24 located on each side plate 22A and 22B. In this way, illumination source 18 can be mounted to and supported by another surface. In one embodiment, mounting holes 24 do not go all the way through the side plates 22A and 22B, in order to prevent sources of unwanted internal reflections, and sources of external light.

In one embodiment, illumination source 18 is comprised of a single row of LED lights (LEDs) 25 mechanically and electrically connected to a circuit board 26, such that the emission centerline of each LED passes through, and is perpendicular to, the longitudinal center line of focusing element 29. In the embodiment shown in FIGS. 1A and 1B, back cover plate 21 has an access hole 27 through which wires can be placed in order to connect the circuit board 26 to the capacitor box 19. For simplicity, only ten (10) LEDs 25, each having an individual lens, are shown, although any suitable number of LEDs 25 can be used. In one embodiment eight (8) LEDs 25, each having an individual lens, and located in a straight line are used. In another embodiment, fifteen (15) LEDs 25, each having an individual lens, and located in a straight line are used. In these embodiments, LEDs 25 are essentially point sources of light along a single line or row, each of which emit rays which diverge from the center line of the LED (call this direction Z) approximately equally in the two directions (X and Y) orthogonal to the centerline of propagation (direction Z) of each towards diaphragm 60 and focusing element 29. (In a more rigorous description, X and Y are actually directions approximately on the surface of a spherical wavefront centered at the LED.)

In yet another embodiment, an LED line source is used for LED 25. (E.g., an LED having a continuous and substantial light-emitting length in the X direction—corresponding to the width of the sheet of light which is desired, e.g., in one embodiment approximately two inches—and a minimal length in the Y direction, e.g., less than approximately 0.5 mm. Such an LED is implemented electrically either as a single LED, or as a series- and/or parallel-connected plurality of LEDs.) In one such embodiment, a cylindrical lens or other focusing element is used proximate to the LED line source in order to direct and evenly spread the light toward focusing element 29.

Figure 7:
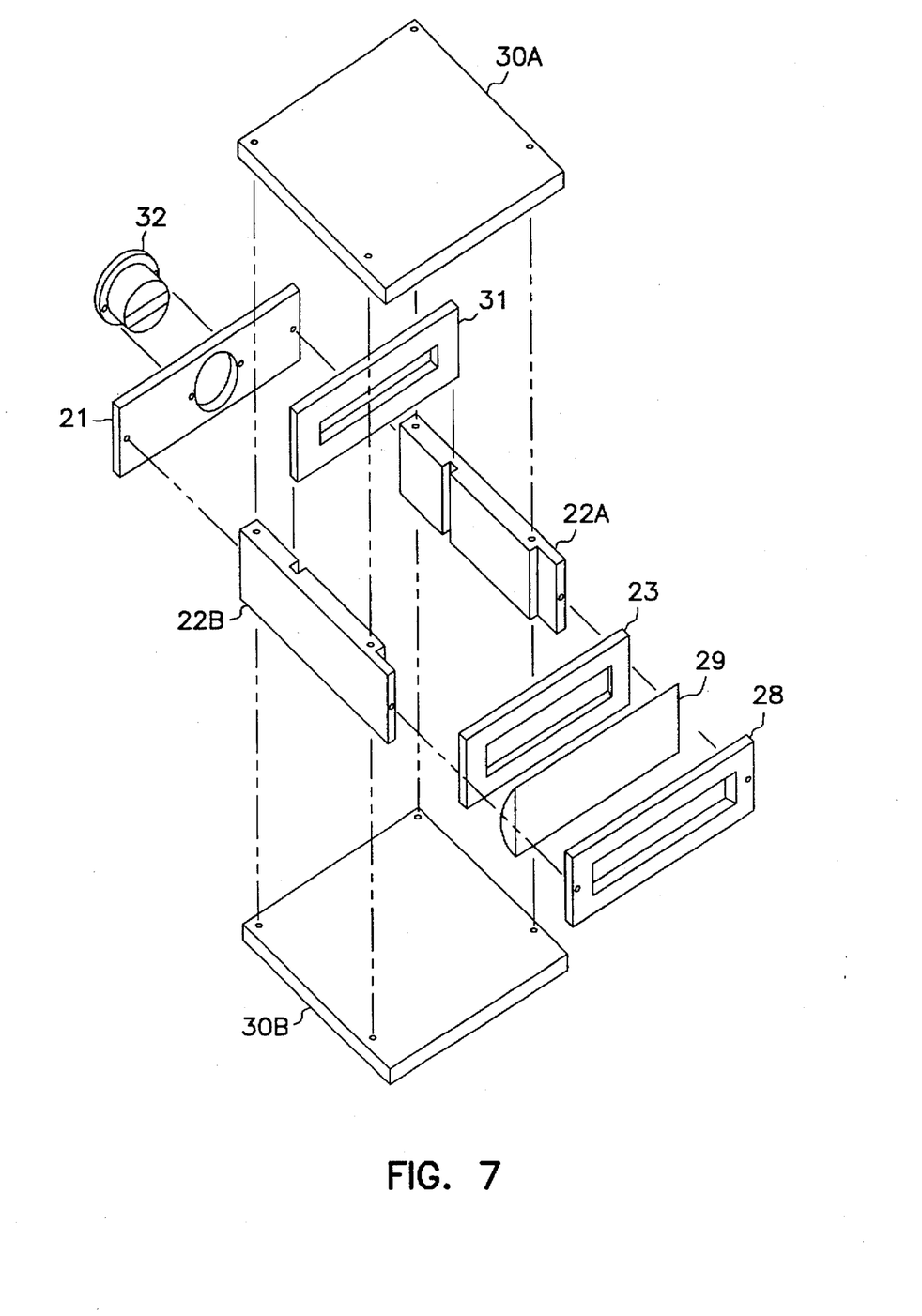
FIG. 7 is a blow-up isometric view of an alternative embodiment of the present invention wherein a xenon flashlamp 32 and a slit diaphragm 31 are used.

Yet another embodiment of the present invention, as shown in FIG. 7, uses a xenon strobe light source 32, e.g., a linear short-arc flashlamp bulb such as an EG&G model FX-108B-type tube, and a backplane slit diaphragm 31 in place of the row of LEDs 25. In one such xenon strobe embodiment, a color filter is also placed in series with the light path in order to obtain a monochromatic light, which can be more sharply focused than white light.

In yet another embodiment, two or more rows of LEDs 25 are used for LEDs 25. For example, in one embodiment, two parallel rows of LEDs are placed on circuit board 26 in order to create two parallel wedges of light. In one such embodiment different color light sources are used, e.g., fifteen tightly spaced red-color LEDs 25 are used for the first row, and fifteen tightly spaced green-color LEDs 25 are used for the second row which is spaced (for example, by 0.1 inch) in the Y direction from the first row, in order that each wedge of light generated has a different color to be distinguished by imaging device 14. In another such embodiment, each row of LEDs 25 is strobed at a different time, in order that each wedge of light can be distinguished by imaging device 14 by which timing pulse, and thus which LED row, was active. In yet another embodiment, one row of LEDs is displaced in the Z direction as well as in the Y direction on order to adjust the relative shape and/or displacement of the wedges of light generated; in other embodiments, a row of infra-red LEDs and a row of red, yellow, green or blue LEDs are useful because the focal length of a cylindrical glass lens-type focusing element 29 is different at infra-red wavelengths than at red, yellow, green or blue wavelengths, and thus two parallel planes separating light from dark, one infra-red and the other red, for example, can be generated, since the displacement between the starting line of the planes is defined, at least in part, by the Y-direction displacement between the two rows of LEDs, and the ending line at the two respective focal lines is determined, at least in part, by the difference in focal lengths at the two wavelengths.

The width of LED(s) 25 in the X direction can be of any suitable width, and in one embodiment, approximately corresponds to the corresponding X-direction width of opening 40 of outside diaphragm 23 (or of opening 42 of inside diaphragm 28), e.g., from one inch or shorter, to one foot or longer. Preferably, focusing element 29 is made longer and wider than the corresponding respective lengths and widths of the openings 40 and/or 42 in order that reflections and/or dispersions of light from the ends and edges, respectively, of focusing element 29 are minimized.

The LEDs are of any suitable and available color, such as infra-red, red, amber, yellow, green, or blue, which provides satisfactory illumination for the relatively small aperture or f-stop needed on the imaging device 14 being used. In one embodiment, LEDs 25 are a high-brightness red which have a brightness of about 1200 millicandles (mcd) at a peak wavelength of approximately 621 nm. In one such embodiment, the high-brightness red LEDs used for LEDs are HLMA-KH00-type T1-sized lights having a half-angle of approximately 22.5° available from Hewlett-Packard. In another embodiment, LEDs 25 are infra-red with a brightness of about 220 mcd at 600 milliWatt pulsed, having a peak wavelength of about 850, 880 or 940 nm. The use of infrared light is desirable for some embodiments because it reduces the risk of exposing nearby workers to over-bright or blinding light; in other embodiments, infra-red LEDs are useful because the focal length of a cylindrical glass lens-type focusing element 29 is different at infra-red wavelengths than at red, yellow, green or blue wavelengths. In yet another embodiment, LEDs 25 are amber or orange-colored with a peak wavelength of about 592 nm. Even though the wavelength of amber LEDs is closer to the peak wavelength of certain solid state imaging devices (i.e., 550 nm) than is the wavelength of the high-brightness red or the infra-red LEDs, the illumination which is provided with red LEDs tends to provide better and sharper images for certain objects 16. It is expected that as high-brightness LEDs having shorter wavelengths and/or a sharper peak wavelength become available, it will be advantageous to use one or both of these characteristics in order to provide a sharper edge to the light pattern generated. The wavelength of LEDs 25 may be chosen for their ability to illuminate certain objects, or for camera sensitivity, or for measurement accuracy.

In the embodiment shown in FIGS. 1A and 1B, focusing element 29 is placed parallel to and between a front straight-edged diaphragm 23 and a back straight-edged diaphragm 28, both of which preferably have a flat black surface to prevent reflections. Furthermore, the inner, light-defining edges of both diaphragm openings are beveled to a sharp edge in order to reduce reflections from these edges. The flat black surface can be obtained by either painting or anodization as described above. In the embodiment shown in FIGS. 1A and 1B, diaphragms 23 and 28 are very thin, preferably less than one (1) mm, and can be made from any suitable material, such as aluminum, steel, or plastic. In one embodiment, the enclosure for illumination source 18 is injection molded of plastic.

In one embodiment, focusing element 29 is coated on one or both surfaces with an anti-reflective coating (anti-reflective at the peak wavelength of LEDs 25) in order to reduce reflections and produce a cleaner, sharper edge to the projected light.

Either or both the front straight-edged diaphragm 23 and the back straight-edged diaphragm 28 serve to provide delineation between the areas which are illuminated (e.g., pins 17) and the areas which are not (e.g., socket 16). By having the edge of diaphragm 23 located at the plane of light defined by diaphragm 28, the plane which separates dark from light is further enhanced. Specifically, the top portion of both the front straight-edged diaphragm 23 and the back straight-edged diaphragm 28 serve primarily to reduce unwanted or secondary reflections in the focusing element 29. These secondary reflections occur when the focusing element 29 reflects degrading rays back to its own upper surface, resulting in undesirable vertical rays. The lower portions of both the front straight-edged diaphragm 23 and the back straight-edged diaphragm 28 are necessary to provide a clean edge on the ray projecting across the object.

In another embodiment of the present invention, illumination source 18 has only a back straight-edged diaphragm 28 parallel to the focusing element 29 to delineate between areas which are illuminated and those which are not. In this embodiment, diaphragm 23 has a larger opening and is used primarily to keep focusing element 29 in place.

In yet another embodiment of the present invention, illumination source 18 has only a front straight-edged diaphragm 23 parallel to the focusing element 29 to delineate between areas which are illuminated and those which are not. In this embodiment, diaphragm 28 has a larger opening and is used primarily to keep focusing element 29 in place.

Figure 2:
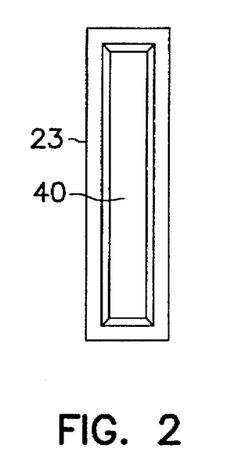
FIG. 2 is a side view of a front straight-edged diaphragm of an embodiment of the present invention.

FIG. 2 is a front view of the front straight-edged diaphragm 23 which can be any size sufficient to delineate between illuminated areas and non-illuminated areas. In one embodiment it has a length of about ten (10) cm and a width of about two (2) cm, with an inside rectangular opening 40 of about 7.5 cm by about one (1) cm. In another embodiment, front straight-edged diaphragm 23 has a length of about 13 cm and a width of about two (2) cm, with an inside rectangular opening 40 of about ten (10) cm by about one (1) cm.

Figure 3:
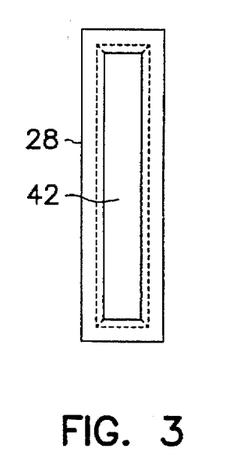
FIG. 3 is a side view of a back straight-edged diaphragm of the present invention.

FIG. 3 is a front view of the back straight-edged diaphragm 28 which can be any size sufficient to delineate between illuminated areas and non-illuminated areas. In one embodiment it has a length of about nine (9) cm and a width of about two (2) cm, with an inside rectangular opening 42 of about 7.5 cm by about one (1) cm. In another embodiment, back straight-edged diaphragm 28 has a length of about 11.5 cm and a width of about two (2) cm, with an inside rectangular opening 40 of about ten (10) cm by about one (1) cm.

Figure 6:
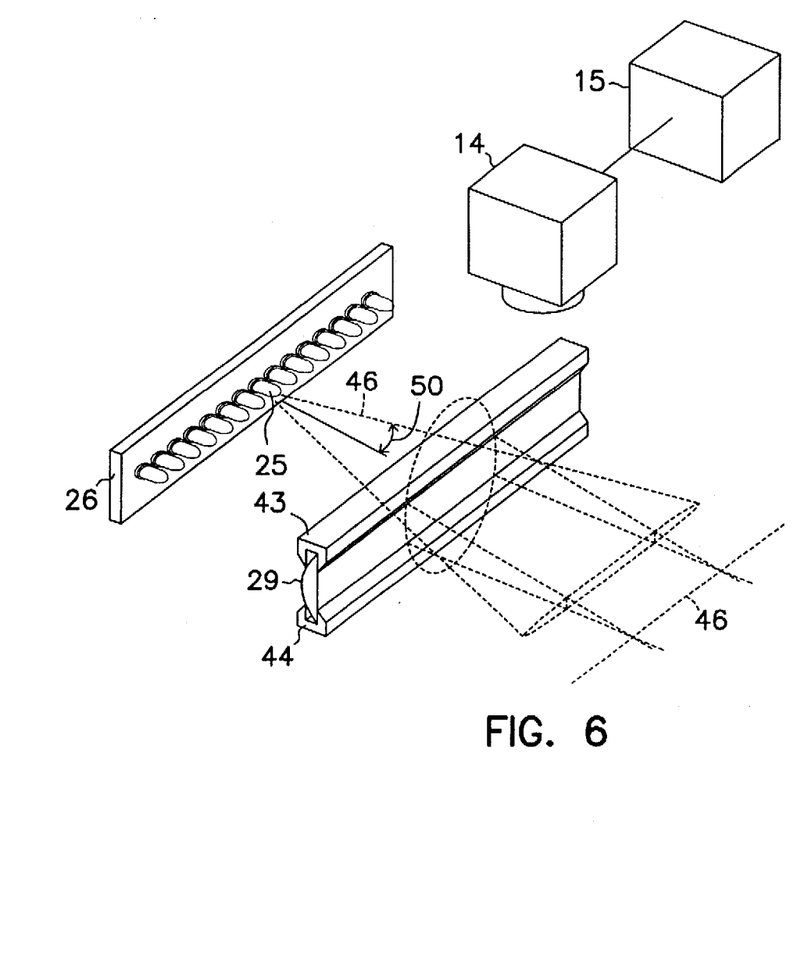
FIG. 6 is a cut-away isometric view of one embodiment of the present invention wherein two U-shaped diaphragms are used.

An isometric view of focusing element 29 together with the LEDs 25 is shown in FIG. 6. In one embodiment, focusing element 29 is a plano-convex cylindrical lens (in one such embodiment, a plano-convex cylindrical lens is used) wherein light rays from the LEDs 25 are focused in a first (e.g., horizontal) direction or dimension and are not focused in a second, orthogonal (e.g., vertical) direction or dimension. In an alternative embodiment, focusing element 29 is a Fresnel-type lens which focuses in a manner similar to a cylindrical lens in the first direction and not in the orthogonal direction. In another alternative embodiment, focusing element 29 is a phase-grating-type optical element which focuses in the first direction and not in the orthogonal direction. In another embodiment, focusing element 29 is a holographic-type optical element which focuses in the first direction and not in the orthogonal direction. In yet another alternative embodiment, focusing element 29 is a mirror-type optical element which focuses in the first direction and not in the orthogonal direction.

In one embodiment which uses a cylindrical lens having a curved face and a flat face for focusing element 29, the curved surface of the focusing element 29 preferably faces inwardly, i.e., towards the row of LEDs 25, and the flat surface faces in an outward direction. In another embodiment, a cylindrical lens, such as an acrylic rod, having a circular cross-section, and thus a very short focal length, is used for focusing element 29. In one such embodiment, such a rod is milled flat on the top and bottom (next to diaphragms 43 and 44, respectively) to save space. In one embodiment, LEDs 25 are parallel to the focusing element 29 and separated a suitable distance from the focusing element 29 so that the rays from the LEDs 25 are focused into one line. In one embodiment, LEDs 25 are about five cm. to about eight cm. from the focusing element 29. If the LEDs 25 are placed too close to the focusing element 29, the projected illumination may cause unwanted illumination. For example, in the embodiment shown in FIGS. 1A and 1B, the white plastic of the socket of object 16 can also become illuminated. This excess illumination on the white plastic of the socket 16 is noise to the signal of interest, i.e., the image of the pin tips of pins 17, and can result in a condition known as bloom, wherein the image produced by imaging device 14 becomes merely a bright white signal, or has such a poor signal-to-noise ratio. In contrast, if the LEDs 25 are placed too far from the focusing element 29, the rays of light become more parallel in the horizontal direction, which causes shadowing, and the illumination can be too dim for adequate inspection Lens faults can occur due to the inherent nature of light or to the inefficiency of the lens itself. In the camera art, "flare" is caused by reflections from surfaces within the lens body and/or camera body, and causes an overall loss of contrast. If not compensated for, similar problems can occur in the light projected from illumination source 18, and therefore one embodiment of the present invention uses anti-reflective surfaces inside illumination source 18. A lens hood on imaging device 14 partly overcomes the camera problem by cutting down the light that does not play a part in forming the image. More corrections are attainable with lens coatings, which are on nearly all modern camera lenses, and are used in one embodiment on both the lens of imaging device 14 and on focusing element 29. The coatings work by setting up a second reflection from the lens surface that interferes with the original reflection, thereby nearly cancelling it out. This is a principle known as "destructive interference."

"Chromatic aberration" is where a lens focuses different wavelengths of light at different focal points. "Spherical aberration" occurs when light from the edges of a circularly-curved lens are focused at different distances that light through the center of the lens. Circularly curved lenses are used since they are cheaper to produce a lens with a spherical curved surface than one in which the curvature changes. The problem, however, is that spherical aberration can occur, where the edges of the lens focus the light waves at a different point from the center of the lens, causing lack of sharpness. Regarding the oblique rays passing through the lens, these fall on different parts of the "image plane," in a blur rather than being superimposed. This slightly different aspect of spherical aberration is called coma. To overcome this can be costly, but mirror-type focusing elements 29 do not suffer from these aberrations.

Figure 4A:
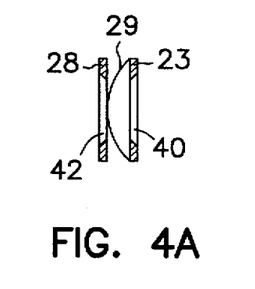
FIGS. 4A, 4B are side views of focusing element 29 with two diaphragm arrangements, the arrangement of FIG. 4A providing more light, and the arrangement of FIG. 4B providing a sharper edge between light and dark regions.
Figure 4B:
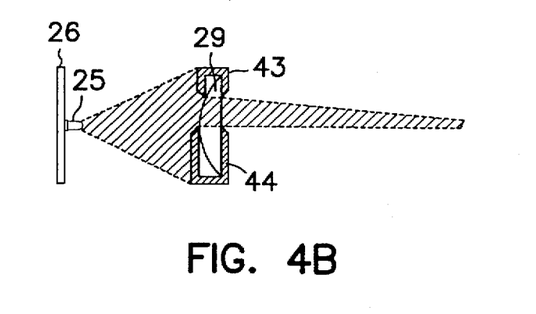

FIG. 4A shows an end view of a cylindrical lens-type focusing element 29 surrounded by back diaphragm 28 having opening 42 and front diaphragm 23 having opening 40. FIG. 4B shows an end view of a cylindrical lens-type focusing element 29 surrounded by top diaphragms 43 (comprising both an inner and an outer diaphragm) and bottom diaphragms 44 (comprising both an inner and an outer diaphragm), and wherein the edges of the diaphragms 44 define edges substantially at the centerline of the cylindrical lens in order to achieve a sharp plane edge right at the centerline of the light emitted from LEDs 25, and thus avoid the distortion (which corresponds to spherical aberration on a spherical lens) which results from using a circularly-curved cylindrical lens, and the distortion (which corresponds to coma in a spherical lens) which results from rays which enter the lens at an oblique angle. Chromatic aberration is generally not an issue when using LEDs 25 as the light source, but this situation does need to be addressed (such as by using a monochromatic filter) when using a xenon light source 32 and slit diaphragm 31, which otherwise has a wide spectral distribution. In one embodiment, a color filter (e.g., a monochromatic filter which passes a narrow band of wavelengths) is used in the light path (either inside the illumination source 18 of FIG. 7, such as at the plane of slit diaphragm 31, or outside, such as at the outside flat surface of focusing element 29, or in both places), in order to reduce the effects of chromatic aberrations.

Figure 5A:
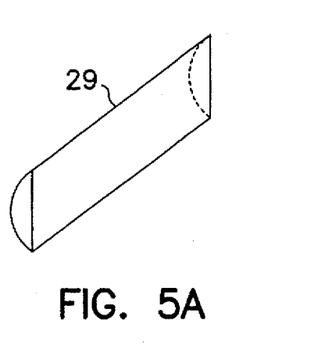
FIGS. 5A, 5B are an isometric view, an end view, a front view, and a side view, 5C, and 5D respectively, of a lens used for focusing element 29 of one embodiment of the present invention
Figure 5B:
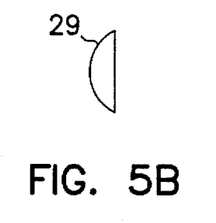
Figure 5C:
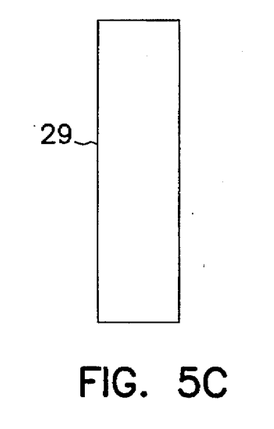
Figure 5D:
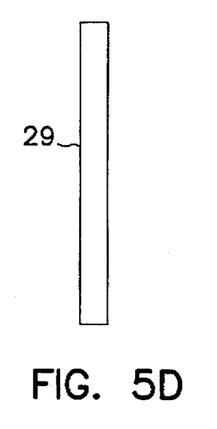

FIG. 5A shows an isometric view, FIG. 5B shows an end view, FIG. 5C shows a front view, and FIG. 5D shows a side view, all of one embodiment of the focusing element 29 wherein the length is about 8.5 cm. In one embodiment, all the edges of the lens are ground to reduce mechanical stress in the lens. In one such embodiment, an Edmund Scientific stock number N32,729 is cut in half, providing a glass piano-cylindrical lens with a focal length of 25 mm, a centerline length on the flat face of approximately 85 mm, and a width of approximately 19 mm is used for focusing element 29.

FIG. 6 shows an isometric view of another embodiment of the present invention wherein there is a U-shaped top diaphragm 43 and a U-shaped bottom diaphragm 44, both having bevelled ends and sharp edges. The U-shaped top diaphragm 43 provides two light-defining edges, one on either side of lens 29, and serves primarily to reduce unwanted or secondary reflections in the focusing element 29 as described above. The U-shaped bottom diaphragm 44 also provides two light-defining edges, one on either side of lens 29, and is used to provide a clean edge, fixed in the Y direction, which extends along the X direction, on the rays projecting in the Z direction across the object 16 (thus defining a plane in the X-Z directions above which there is diffuse light, and below which there is little or no light). In one embodiment, both diaphragms 43 and 44 have edges which are parallel to the central axis of focusing element 29. The bevelled ends and edges of diaphragms 43 and 44 come to a sharp edge in order to further reduce any reflections from these edges. In the embodiment shown in FIG. 4B, the parallel edges of lower diaphragm 44 are placed at or very near the longitudinal centerline of lens 29 (which is also at or very near, and perpendicular to, the propagation centerlines of the LEDs 25).

FIG. 6 also shows how the rays 46 from one representative LED 25 diverge broadly at a suitable angle 50 to form a circle of light 48 much larger than the width of focusing element 29 as defined by the diaphragms 43 and 44. The presence of lens 29 and one or more diaphragms, each having one or more sharp edges, such as 43 and 44, causes the rays 46 themselves to have a sharp truncated edge as they are focused by lens 29 and projected across object 16 and electrical connectors 17. In one embodiment, the ½ angle of the rays 46 is about 22.5° from the centerline, so that the viewing angle is about 45°, which provides an approximately optimum distance/intensity/size tradeoff. After passing through the focusing element 29, rays 46 form a flattened oval 52 truncated at the top and bottom by straight-edge diaphragm in the horizontal direction. The rays 46 from all of the LEDs 25, therefore, result in a row of overlapping truncated ovals which are focused so that they nearly become a line at the focal line 48 of focusing element 29, and the truncation provided by diaphragm 44 and lens 29 forms a plane extending between diaphragm 44 and focal line 48; below this plane there is no light, above this plane there is light coming from multiple directions. In one embodiment, shown in FIG. 4B, diaphragm 44 extends up to approximately the longitudinal center line of lens 29, and the emission centerline of each LED 25 pass through and are perpendicular to this longitudinal center line, in order to produce a sharper edge on the plane separating light from dark in the propagated light; a tradeoff is that the resultant beam is not quite as bright in certain areas as in the beam generated when the edge of the diaphragm is further from the center line of lens 29.

In another embodiment of the present invention, there is only a U-shaped bottom diaphragm having bevelled ends and sharp edges, positioned parallel to and between the LEDs and the lens.

FIG. 7 shows yet another embodiment of illumination source 18 of the present invention, wherein a xenon strobe light source 32, e.g., a linear short-arc flashlamp bulb such as an EG&G model FX-108B-type tube, and a backplane slit diaphragm 31 are used in place of the row of LEDs 25. In one such embodiment, the opening in backplane slit diaphragm 31 is approximately 0.25 inch wide and 3 inches long, the opening in diaphragms 23 and 28 are each 0.5 inch wide and 4.0 inches long. In one such xenon strobe embodiment, a color filter is also placed in series with the light path at slit diaphragm 31 in order to obtain a monochromatic light, which can be more sharply focused than white light.

Figure 8:
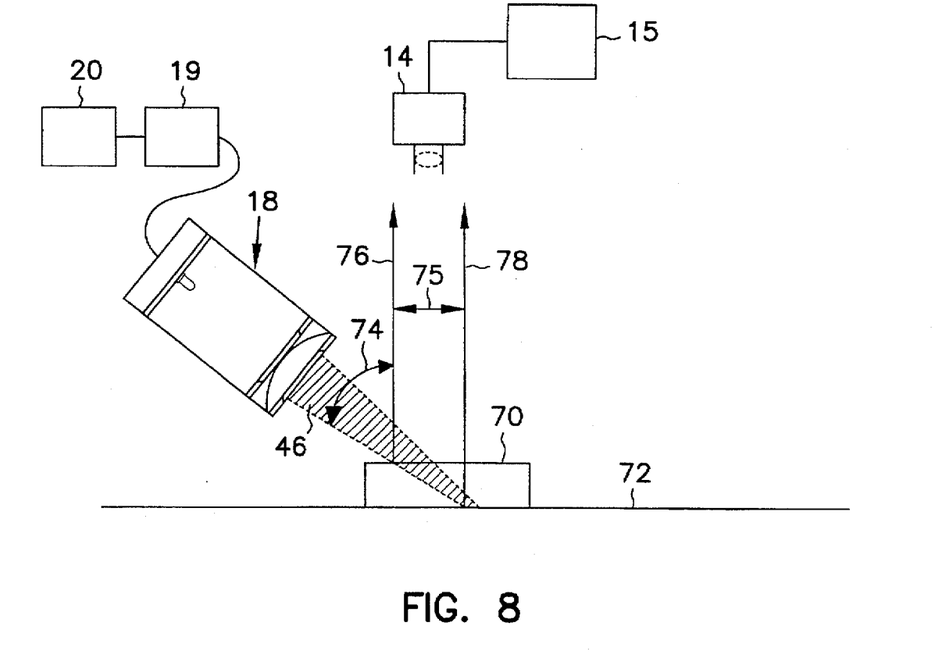
FIG. 8 is a schematic diagram of a side view of one embodiment of the present invention wherein the height of a raised surface can be determined.

FIG. 8 shows another alternative use of the present invention. In FIG. 8, illumination source 18, imaging device 14, and image processor 15, comprise machine-vision system 100 used to determine the height of object 70 on a flat plane 72. Specifically the rays 46 from illumination source 18 are shined at a given angle 74 towards the raised surface 70. The horizontal displacement 75 between edges of the first vertical reflection 76 originating from the top of the raised surface 70 and second vertical reflection 78 originating from the bottom of the raised surface 70 is then measured. In this way, the height of the raised surface 70 can then be calculated by image processor 15. This calculation can be calibrated using objects at known and/or measured heights from a surface.

Figure 9:
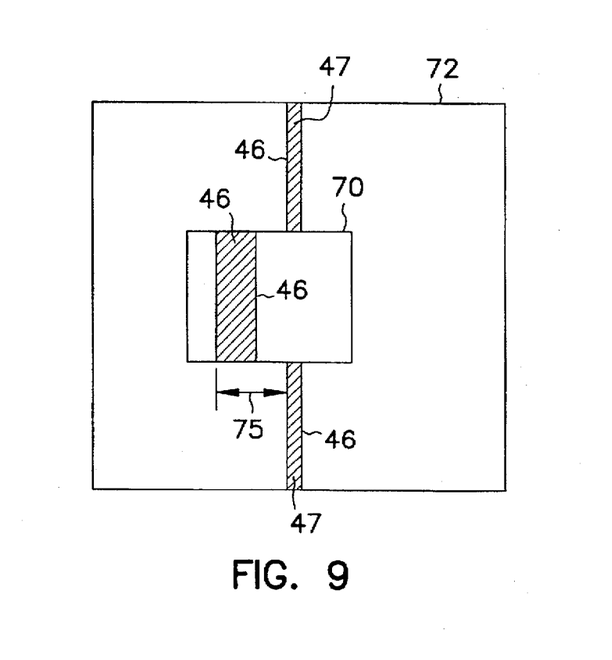
FIG. 9 is a schematic diagram of the view from imaging device 14 of the embodiment of FIG. 8 wherein the height of the raised surface can be determined.

FIG. 9 shows the view from imaging device 14 of object 70 on flat plane 72 as in FIG. 8, wherein the rays 46 are displaced in one direction such that the height of the raised surface 70 can be calculated.

Figure 10:
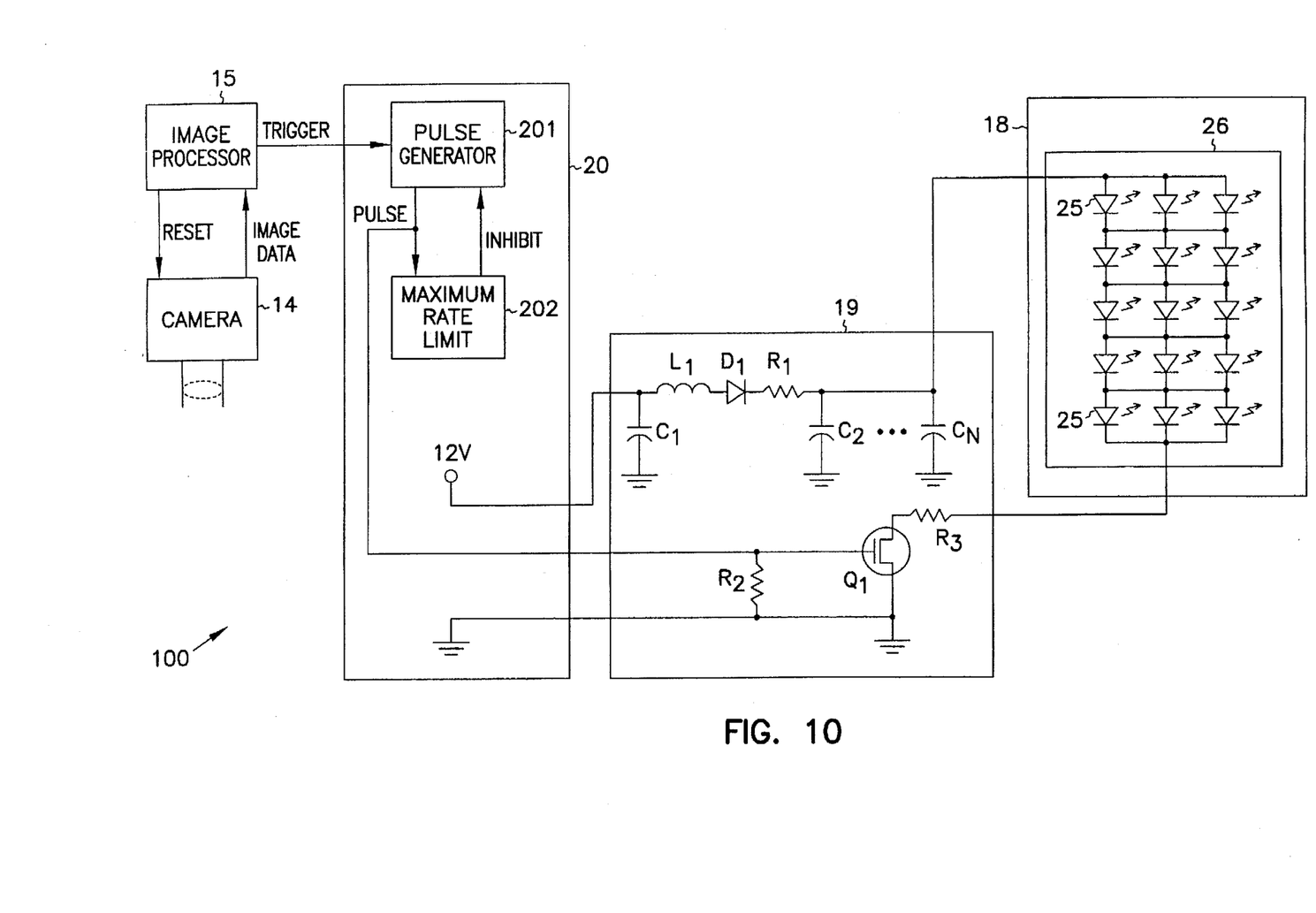

FIG. 10 is a block diagram of the electrical connections for one embodiment of machine-vision illumination system 100. Image processor 15 sends a reset signal to imaging device 14, then (or simultaneously) sends a trigger signal to power supply 20. Within power supply 20, the trigger signal activates pulse generator 201 to generate a control pulse of a predetermined length. The control pulse is used to turn on transistor Q1 to generate a flash on LEDs 25, which is current-limited by resistor R3. The control pulse also activates the maximum-rate-limit circuit 202, which inhibits any further control pulses from pulse generator 201 for a predetermined amount of time. The 12 volt signal from power supply 20 is filtered by the low-pass filter comprising C1, L1, D1, and R1, and charges capacitors C2 through $C_N$ (in one embodiment, N is 12). In one such embodiment, C1 through C12 are each 2200 µF, L1 is 40 µH iron-core, D1 as a 1N4001 diode, and R1 is a 0 ohm conductor. C2 through $C_N$ are discharged through fifteen LEDs 25, which in this embodiment are wired in a parallel-series manner as shown, and R3 and Q1, as activated by the above-described control pulse. In one such embodiment, R3 is replaced by a zero-ohm conductor, and the voltage drop across the LEDs and Q1 is used to self-limit the current through the LEDs. The control pulse is fed across resistor R2, which in one embodiment is 100 KΩ, to develop the necessary voltage for driving transistor Q1, which in this embodiment is a MTP75N05HD MOSFET.

Figure 11:
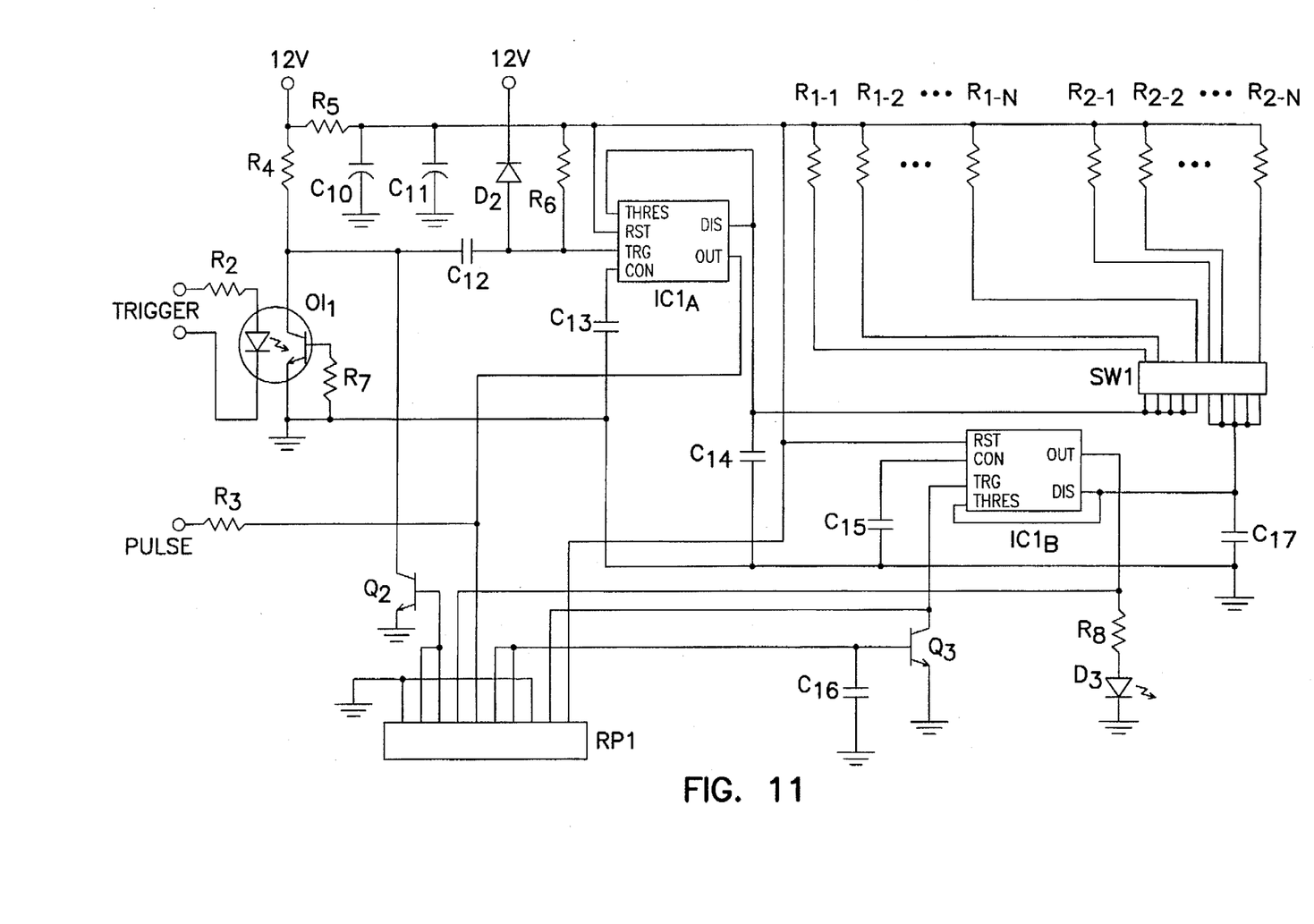
FIG. 11 is a schematic diagram of power supply 20.

FIG. 11 is a more-detailed schematic diagram of power supply 20. The input trigger is fed through resistor R2 to drive the input of opto-isolator OI1. The output of opto-isolator OI1 is coupled through capacitor C12 (and the associated circuit R4, R6 and D2) to the TRG input of timer circuit $1C1_A$. (In one embodiment, timers $1C1_A$ and $1C1_B$ are each ½ of a 556-type dual timer.) The timing constant of timer $1C1_A$ is set by C14 and R1-x, (where x is selected from 1 through N), and determines the pulse width of the control pulse driving Q1, and thus the LEDs. In one embodiment, five selectable pulse widths are predetermined and selected by SW1, which is a five-way exclusive dual-pole-single-throw switch, wherein one resistor of the set R1-1 through R1-N is selected for connection to the DIS input pin of $1C1_A$, and a corresponding one resistor of the set R2-1 through R2-N is selected for connection to the DIS input pin of $1C1_B$. The timing constant of timer $1C1_B$ is set by C17 and R2-x, (where x is selected from 1 through N), and determines the minimum time between control pulses driving Q1, and thus the LEDs. In one embodiment, the five selectable predetermined pulse widths are 25 microseconds (µs), 50 µs, 100 µs, 200 µs and 500 µs; the corresponding maximum pulse rates controlled by maximum rate limit circuit 202 are 200 Hz, 120 Hz, 60 Hz, 30 Hz, and 10 Hz, respectively, and are predetermined and selected by SW1. Thus, in the embodiment which uses a 60 Hz camera image rate, 100 µs-long control pulses are used to activate LEDs 25. In one embodiment, it is desired to have an average LED illumination intensity of at least ten times the ambient light; thus, when imaging device 14 is taking one frame every 16.7 milliseconds, a 100 microsecond pulse should be at least 1670 times as intense as the ambient light. In one such an embodiment, a shroud is used to reduce the ambient light, and a red filter (substantially transparent to the peak wavelength of illumination source 18) is placed over the lens of imaging device 14 in order to reduce ambient light and pass the light of illumination source 18. The control pulse output signal is driven through resistor R3.

In one embodiment, opto-isolator OI1 is a 4N37-type part, resistor R2 is 100 Ω, resistor R3 is 100 Ω, resistor R7 is 1MΩ, resistor R8 is 1KΩ and visible-color LED D3 indicates when the circuit is active, resistor R4 is 4700 Ω, resistor R5 is 10 Ω, resistor R6 is 10KΩ, diode D2 is a 1 N914, resistor R1-1 is 2.26KΩ, resistor R1-2 is 4.53KΩ, resistor R1-3 is 9.1KΩ, resistor R1-4 is 18.2KΩ, resistor R1-5 is 45.3KΩ, resistor R2-1 is 37.4KΩ, resistor R2-2 is 75KΩ, resistor R2-3 is 150KΩ, resistor R2-4 is 301KΩ, resistor R2-5 is 909KΩ, C14 is 0.01 µF, C17 is 0.1 µF, C12 is 0.001 µF, C10 is 100 µF, C11 is 0.1 µF, C13, C15, and C16 are each 0.01 µF, Q2 and Q3 are each 2N3904 NPN transistors, and RP1 is a 10KΩ resistor pack.

The process of the present invention is unlike conventional illumination sources since it is compact, generates a light source from more than one point source with suitable brightness, focuses the light source into a sharply defined source in one dimension (e.g., horizontally) and a diffuse source in another dimension or dimensions (e.g., vertically, or vertically and longitudinally), so that even extremely small parts can be adequately inspected and accurately viewed or measured with machine-vision system 100. Another aspect of the present invention is to provide a compact illumination source, preferably monochromatic, which can be focused to provide uniform multi-directional light onto objects on one side of an imaginary plane, while minimizing light on the other side of that plane. Another aspect of the present invention is to provide a compact monochromatic LED (light-emitting diode) illumination source, which can be focused to provide uniform multi-directional light onto objects on one side of an imaginary plane, while minimizing light on the other side of that plane. Yet another aspect of the present invention is to have such an LED illumination source be pulsed with a relatively high-power, low duty-cycle power source.

In summary, the apparatus and method of the present invention, preferably having a cylindrically focusing element, is advantageous because it is compact, yet is able to emit light in more than one direction. The present invention also has the advantage of producing a sharper ray of light by having the cylindrically focusing element having a plano-convex cylinder lens arranged, in one embodiment, with the flat face outwards in conjunction with a suitable straight-edged diaphragm or diaphragms. In another embodiment, the flat face of the cylindrical lens is facing inward. A further advantage is achieved by using diaphragms and other components which have a flat black surface to eliminate secondary lines and other undesirable reflections and resultant loss of contrast in the formed image.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. An illumination source for illuminating an object in a machine-vision system the machine-vision system including an imaging device that has an optical axis, comprising:

a light source that emits non-collimated light from a plurality of locations, the locations being on a substantially straight line;

a focusing element, the focusing element focusing light from the light source in one dimension to a focal line, wherein the focusing element is separated from the straight line by a distance sufficient to focus rays from the plurality of locations into the focal line, and wherein there is a light path from the straight line to the focusing element and then to the focal line; and a first diaphragm located in the light path between the light source and the focal line and defining a sharp edge in the rays in order to produce a surface substantially delineating a illuminated volume having light from the light source from an unilluminated volume that has substantially no light from the light source and substantially less light overall, and wherein the optical axis of the imaging device passes through the surface such that a portion of the object viewable by the imaging device lies within the illuminated volume and another portion of the object otherwise viewable by the imaging device lies in the unilluminated volume.

2. The illumination source as recited in claim 1, wherein the first diaphragm has at least one straight-line segment lying substantially within a plane which also contains substantially the surface and the straight line of the light source.

3. The illumination source as recited in claim 2, further comprising an enclosure having an interior surface which is anti-reflective at a wavelength of the light source, the straight line of the light source being located inside the enclosure.

4. The illumination source as recited in claim 3 wherein the focusing element is a plano-convex cylindrical lens having a flat surface and a cylindrical surface.

5. The illumination source as recited in claim 4, wherein the first diaphragm has a straight edge located near the cylindrical surface of the cylindrical lens, and further comprising a second straight-edged diaphragm having a straight edge located near the flat surface of the cylindrical lens to reduce reflections from the light source.

6. The illumination source as recited in claim 1 wherein the light source comprises at least one light-emitting diode (LED) which emits light.

7. The illumination source as recited in claim 6 wherein the light emitted from the LEDs is blue in color.

8. The illumination source as recited in claim 7 wherein the light emitted from the LEDs is at an angle of about 22.5° from a center line of each individual LED.

9. A method for illuminating an object in a machine-vision system the machine-vision system including an imaging device that has an optical axis, comprising the steps of:

(a) emitting non-collimated light from a plurality of locations, the locations being on a substantially straight line;

(b) focusing the emitted light from the plurality of locations into a focal line, and wherein there is a light path from the straight line to a focusing element and then to the focal line; and (c) defining a sharp edge in the rays in order to produce a surface substantially delineating a illuminated volume having light from the light source from an unilluminated volume that has substantially no light from the light source and substantially less light overall, and wherein the optical axis of the imaging device passes through the surface such that a portion of the object viewable by the imaging device lies within the illuminated volume and another portion of the object otherwise viewable by the imaging device lies in the unilluminated volume.

10. The method for illuminating an object as recited in claim 9, wherein the step 2 of defining includes providing at least one straight-line diaphragm segment lying substantially within a plane which also contains substantially the surface and the straight line of the emitted light.

11. The method for illuminating an object as recited in claim 10, further comprising the step of enclosing the straight line and the focusing element with an enclosure having an interior surface which is anti-reflective at a wavelength of the emitted light.

12. The method for illuminating an object as recited in claim 9, wherein the step of emitting comprises emitting light from at least one light-emitting diode (LED).

13. The method for illuminating an object as recited in claim 12, wherein the object is an electrical connector, and further including the step of inspecting an aspect of the connector that affects functionality of the connector.

14. The method for illuminating an object as recited in claim 12, wherein the light emitted from the LEDs is at an angle of about 22.5° from a center line of each individual LED.

15. The method for illuminating an object as recited in claim 9, wherein the focusing element is a plano-convex cylindrical lens having a flat surface and a cylindrical surface.

16. The method for illuminating an object as recited in claim 15, wherein, step of defining includes providing at least a first diaphragm has a straight edge, and the step of placing includes locating the straight edge near the cylindrical surface of the cylindrical lens, and further comprising the step of placing a second straight-edged diaphragm having a straight edge located near the flat surface of the cylindrical lens to reduce reflections from the light source.

17. A machine-vision illumination system, comprising:

an imaging device that has an optical axis;

an image processor coupled to the imaging device; and an illumination source coupled to the image processor, the illumination source comprising:

a light source that emits non-collimated light from a plurality of locations, the locations being on a substantially straight line, a focusing element, the focusing element focusing light from the light source in one dimension to a focal line, wherein the focusing element is separated from the straight line by a distance sufficient to focus rays from the plurality of locations into the focal line, and wherein there is a light path from the straight line to the focusing element and then to the focal line, and a first diaphragm located in the light path and defining a sharp edge in the rays in order to produce a surface substantially delineating a illuminated volume having light from the light source from an unilluminated volume that has substantially no light from the light source and substantially less light overall, and wherein the optical axis of the imaging device passes through the surface such that a portion of the object viewable by the imaging device lies within the illuminated volume and another portion of the object otherwise viewable by the imaging device lies in the unilluminated volume.

18. The machine-vision illumination system as recited in claim 17, wherein the first diaphragm has at least one straight-line segment lying substantially within a plane which also contains substantially the surface and the straight line of the light source.

19. The machine-vision illumination system as recited in claim 18, further comprising an enclosure having an interior surface which is anti-reflective at a wavelength of the light source, the straight line of the light source being located inside the enclosure.

20. The machine-vision illumination system as recited in claim 19 wherein the focusing element is a piano-convex cylindrical lens having a flat surface and a cylindrical surface.

21. The machine-vision illumination system as recited in claim 20, wherein the first diaphragm has a straight edge located near the cylindrical surface of the cylindrical lens, and further comprising a second straight-edged diaphragm having a straight edge located near the flat surface of the cylindrical lens to reduce reflections from the light source.

22. The machine-vision illumination system as recited in claim 17 wherein the light source comprises at least one light-emitting diode (LED) which emits light.

23. The machine-vision illumination system as recited in claim 20 wherein the light emitted from the LEDs is blue in color.

24. The machine-vision illumination system as recited in claim 23 wherein the light emitted from the LEDs is at an angle of about 22.5° from a center line of each individual LED.

* * * * *

UNITED STATES PATENT AND TRADEMARK OFFICE
CERTIFICATE OF CORRECTION

PATENT NO. : 5,745,176
DATED : April 28, 1998
INVENTOR(S) : Gary A. Lebens

It is certified that error appears in the above-indentified patent and that said Letters Patent is hereby corrected as shown below:

Col. 2, line 55, please delete "little, is any" and insert --little, if any--.

Col. 9, line 21, please delete "adequate inspection" and insert --adequate inspection.--.

Col. 10, line 23, please delete "piano-cylindrical" and insert --plano-cylindrical--.

Col. 13, line 39, Claim 1, please delete "system the" and insert --system, the--.

Col. 13, line 55, Claim 1, please delete "a illumination" and insert -- an illuminated--.

Col. 14, line 23, Claim 9, please delete "system the" and insert --system, the--.

Col. 14, line 33, Claim 9, please delete "a illumination" and insert -- an illuminated--.

Col. 14, line 44, Claim 10, please delete "step 2 of" and insert --step of--.

Col. 15, line 2, Claim 16, please delete "wherein, step" and insert --wherein, the step--.
Col. 15, line 27, Claim 17, please delete "a illumination" and insert -- an illuminated--.
Col. 16, line 13, Claim 20, please delete "piano-convex" and insert --plano-convex--.

Signed and Sealed this

Twenty-third Day of November, 1999

Attest:

Q. TODD DICKINSON

*Attesting Officer*    *Acting Commissioner of Patents and Trademarks*